(12) United States Patent
Fischi

(10) Patent No.: US 9,623,163 B1
(45) Date of Patent: Apr. 18, 2017

(54) LEFT VENTRICLE HEART-ASSIST DEVICE

(71) Applicant: Michael Fischi, Fayetteville, NY (US)

(72) Inventor: Michael Fischi, Fayetteville, NY (US)

( * ) Notice: Subject to any disclaimer, the term of this patent is extended or adjusted under 35 U.S.C. 154(b) by 0 days.

(21) Appl. No.: 15/041,845

(22) Filed: Feb. 11, 2016

(51) Int. Cl.
   *A61N 1/362* (2006.01)
   *A61M 1/12* (2006.01)
   *A61M 1/10* (2006.01)

(52) U.S. Cl.
   CPC .......... *A61M 1/122* (2014.02); *A61M 1/1086* (2013.01); *A61M 2230/04* (2013.01)

(58) Field of Classification Search
   CPC ...... A61M 1/122; A61M 1/105; A61M 1/106; A61M 1/1056; A61M 1/1072; A61M 1/1074; A61M 1/1058; A61M 1/1086; A61M 2230/04
   See application file for complete search history.

(56) References Cited

U.S. PATENT DOCUMENTS

| | | | |
|---|---|---|---|
| 4,771,765 A | 9/1988 | Choy et al. | |
| 4,861,330 A | 8/1989 | Voss | |
| 5,139,517 A | 8/1992 | Corral | |
| 5,176,619 A | 1/1993 | Segalowitz | |
| 6,406,422 B1 | 6/2002 | Landesberg | |
| 7,172,551 B2 | 2/2007 | Leasure | |
| 8,221,303 B2 | 7/2012 | Ovil et al. | |
| 8,734,331 B2 | 5/2014 | Evans et al. | |
| 8,849,398 B2 | 9/2014 | Evans | |
| 9,162,017 B2 | 10/2015 | Evans et al. | |
| 2013/0317534 A1* | 11/2013 | Zhou | A61B 17/3207 606/185 |

* cited by examiner

*Primary Examiner* — Mallika D Fairchild
(74) *Attorney, Agent, or Firm* — Bernhard P. Molldrem, Jr.

(57) ABSTRACT

A left-ventricular assist device (LVAD) has a generally ellipsoidal capsule fitted into a patient's ventricle, formed of a cage or frame of shape-memory wire which can be twisted open and shut to expand and collapse a thin membrane, to inflate with the incoming blood during diastole and to contract and squeeze out the blood during systole. A catheter extends from outside the patient's body through a major blood vessel and the patient's aortal valve into the left ventricle. The catheter has an external sheath, an outer tubular shaft onto which proximal ends of the shape-retaining wires are affixed, and a middle shaft extending through the hollow core of the outer shaft and which is affixed to a central shaft of the capsule. A control console has mechanical geared drives coupled to the outer and middle catheter shafts within the catheter. A sensor arrangement synchs action of the LVAD with systole and diastole of the patient's heart.

8 Claims, 3 Drawing Sheets

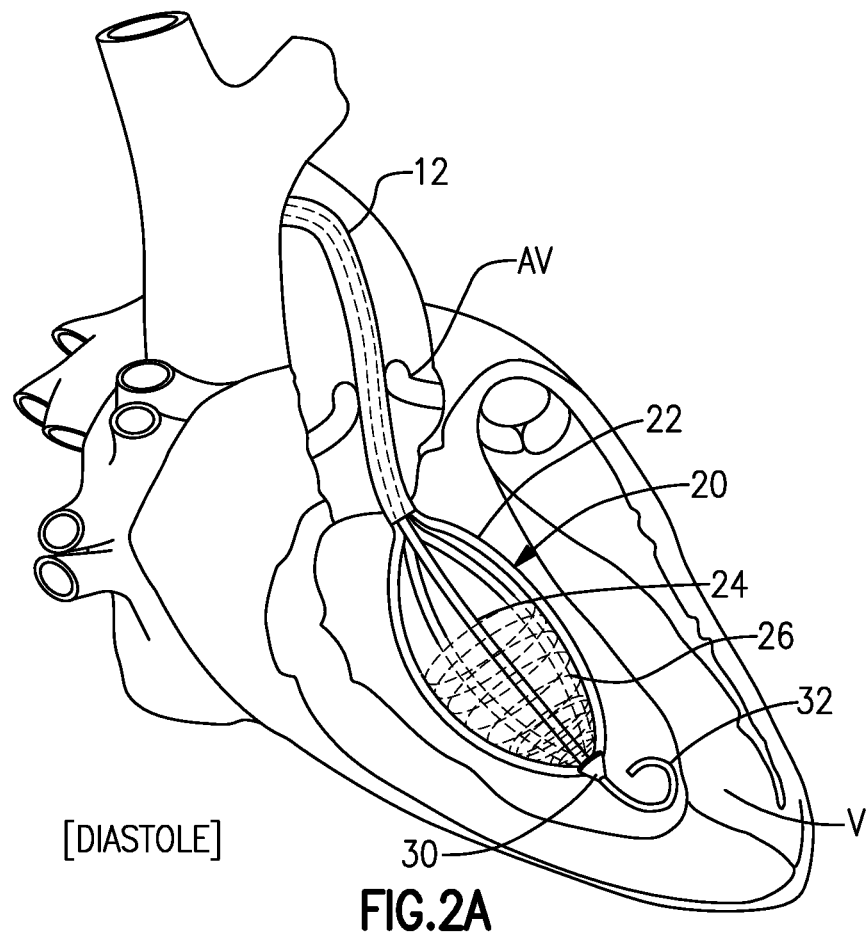
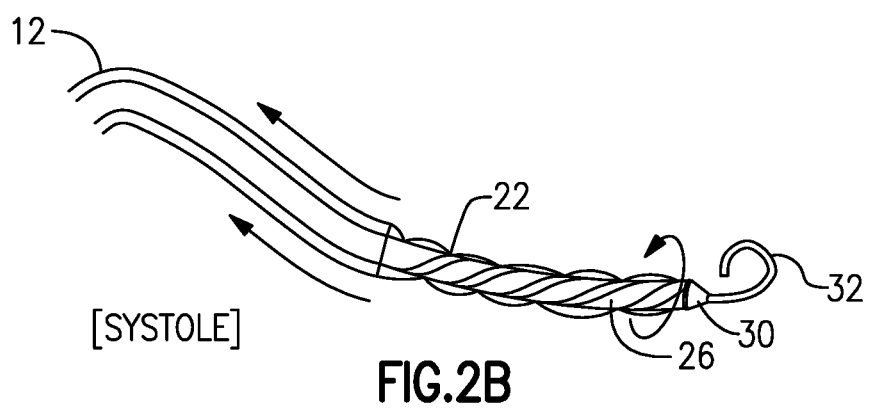

LEFT VENTRICLE HEART-ASSIST DEVICE

BACKGROUND OF THE INVENTION

This invention relates to blood pumps for cardiac support, and is more particularly concerned with an expandable and contractible member to be placed within the ventricular chamber of a patient's heart and which expands and contracts on diastole and systole, respectively, to assist movement of the patients blood into and out of the left ventricle. The invention is also concerned with an endocardial left ventricle assist device or LVAD which does not rely on pumping of air or other fluids to open or inflate the device.

There are pathological conditions that affect the circulatory system, and in particular the heart tissues, which can impair the ability of the heart to pump a normal volume of blood. Injury or disease affecting the muscular tissues of the left ventricle can result in the heart only pumping weakly, or not contracting fully during systole. In order to provide a normal blood flow while a patient's heart is given a chance to heal or improve, there have been several proposals for blood pumps, and in particular intraventricular pumping aids, to help push the patient's blood out of the left ventricle during contraction or systole. Ventricular assist balloon devices, for example, employ a balloon in either the aorta or the left ventricle that inflate in synchronism with the heart's rhythm to squeeze the blood out of the heart and along the aorta. These devices depend on supplying a gas or fluid to inflate and deflate the balloon, and thus can create a risk of injecting gas bubbles directly into the aortic blood. Moreover, these devices are unable to sufficiently augment blood flow in a severely failing hear. Other devices employ an impeller to pump the blood, which can cause hemolysis, among other complications.

It is desired to employ an intracardial LVAD that uses simple rhythmic mechanical motion to drive the pumping mechanism that is placed within the patient's left ventricular cavity to provide a controllable, reliable system to increase blood flow through the patient's system and to compensate for the weakness in the patient's own heart, and to continue the enhanced blood flow during the time of cardiac distress until the patient's condition improves.

OBJECTS AND SUMMARY OF THE INVENTION

Accordingly, it is an object to provide an improved LVAD of a novel and improved design which avoid the problems of the prior art.

A more specific object of this invention is to provide an LVAD that is insertable through a major blood vessel and through the aortal valve directly into the patient's left ventricle, and which is mechanically opened and closed to help pull blood into the left ventricle during diastole and to eject blood from the ventricle and through the aortal valve during systole in a pulsile fashion.

It is a further object to provide an LVAD that can be self-regulating, that is, changing its size or pumping volume depending on changes in ventricular preload.

According to an aspect of the present invention, a left-ventricular assist device employs a capsule that is dimensioned to fit in the ventricular chamber between the aortal valve and the apex of the left ventricle. The capsule has a cage or frame of Nitinol wires or other similar shape-memory metal wire that are in the shape of a elongated ovoid or ellipsoid, which can be twisted open and shut to expand and collapse a thin membrane to inflate with the incoming blood during diastole and to contract and squeeze out the blood during systole.

In a particular embodiment of this invention, as described, a capsule is shaped and dimensioned to occupy the space within the left ventricle of a patient's heart. The capsule has a proximal end and a distal end, the distal end being adapted to reside adjacent the apex of the patient's left ventricle with the proximal end facing towards the aortal valve. The capsule's wire cage is formed of a plurality of shape-retaining or shape-memory resilient wires which each extend from the proximal end to the distal end of the capsule. A central shaft within the cage extends generally axially from the proximal end to the distal end of the wire cage and includes a flange member at the distal end of the central shaft, to which the distal ends of the shape-retaining resilient wires are affixed. A cup is formed of a flexible but inextensible membrane affixed onto the wires at a distal half of the wire cage, leaving the proximal half of the wire cage uncovered, that is, open to receive and discharge blood.

A catheter extends from outside the patient's body through a major blood vessel (typically the patient's femoral artery) and through the patient's aortic valve into the left ventricle. The catheter has an external sheath, and within the sheath there is (at least) an outer tubular shaft onto which the proximal ends of the shape-retaining resilient wires are affixed, and a middle shaft extending through the hollow core of the outer shaft, and which is affixed to the proximal end of the central shaft of the capsule.

A control mechanism, e.g., a control console, has mechanical geared drives coupled to the outer and middle shafts within the catheter, and employs sensors, for example, either pressure sensors within the capsule portion of the LVAD or electrocardial sensors adhered to the patient's chest, sensing systole and diastole of the patient's heart. A drive mechanism imposes a rotation of the inner flange- or disk-bearing shaft with simultaneous foreshortening of the outer shaft that bears the wires of the cage, resulting in a combined "wringing" effect that expels blood out of the aortic valve during systole. The opposite motion is performed during diastole to expand the wire cage and rotate the inner flange or disk in the opposite direction, which expands the capsule; thus facilitating blood entry into the ventricle during diastole.

Favorably, the flange member can be a disk affixed at the distal end of the central shaft.

The LVAD can further include an inner tubular shaft extending through middle tubular shaft and through an open core of said central shaft, with an end cap positioned on said inner shaft on a distal side of the flange member. The end cap may include a soft-rubber tip positioned on its distal side to prevent injury to the heart tissues at or near the apex of the ventricle.

In the embodiments of this invention, cardiac output is augmented by the blood being ejected by the contractile element, to wit, the capsule, as the cup or pocket is foreshortened and twisted by combined effect of the Nitinol (or other pre-shaped metal or polymer) wires being retracted against the fixed axle that is constituted by the central shaft. The flange or disk at the distal end turns to wring the cup or pocket.

The size of the capsule can be adjusted to accommodate larger or smaller hearts by varying the length of the fixed axle, contractile wires, and degree of rotation of the distal flange or disk.

Cardiac output is also enhanced by an "entrainment" effect. That is, the high velocity of the jet of blood ejected by the LVAD creates a relative low-pressure zone adjacent to the high velocity stream, and this draws the adjacent blood out with it. Thus, the cardiac output during each systole is augmented beyond the volume of the contractile element or capsule alone.

Likewise, diastolic intake is augmented by the expansion of the contractile element or capsule by creating a relative vacuum that facilitates by suction inflow of blood through the mitral valve.

While the described embodiment is designed and configured to be inserted into the left ventricle, an assist device of similar construction could be positioned outside the heart proper and within the aorta. Also, in some cases a ventricular assist device of this same general design could be used in the patient's right ventricle to assist in pulmonary blood flow. The capsule could also be positioned in the aorta.

The device(s) of this invention can be self-regulating by controlling the size, i.e., amount of opening and closing of the capsule, depending upon changes in preload.

Systole, diastole, preload and afterload can be sensed by a combination of electrical timing via ECG techniques, and also using pressure transduction techniques with a sensor at the tip of the catheter (within the ventricle). The size and timing of the LVAD device can potentially be dynamically controlled to adjust on a beat-to-beat basis. In case multiple premature ventricular contractions or PVC's are detected, the capsule can be contracted down until the heart's arrhythmia ceases.

The LVAD and associated catheter can be installed in a known fashion over a guide wire that is inserted first via the patient's femoral artery and through the aorta and aortic valve into the ventricle. Radio-opaque markers on the shaft of the catheter and at the distal end of the capsule can assist in positioning the capsule at or near the apex of the ventricle and with the proximal end at a suitable position relative to the aortic valve annulus.

These and other objects, features, and advantages of the invention will become apparent from the following detailed description of selected preferred embodiments, which is to be read in connection with the accompanying Drawing:

BRIEF DESCRIPTION OF THE DRAWING

FIG. 2A is a cut away view of the patient's heart showing the LVAD of this embodiment during diastole or expansion of the left ventricle.

FIG. 2B is a perspective view of the capsule of the LVAD of this embodiment in a compressed state as would occur during systole of the patient's heart.

DETAILED DESCRIPTION OF THE PREFERRED EMBODIMENT

Figure 1:
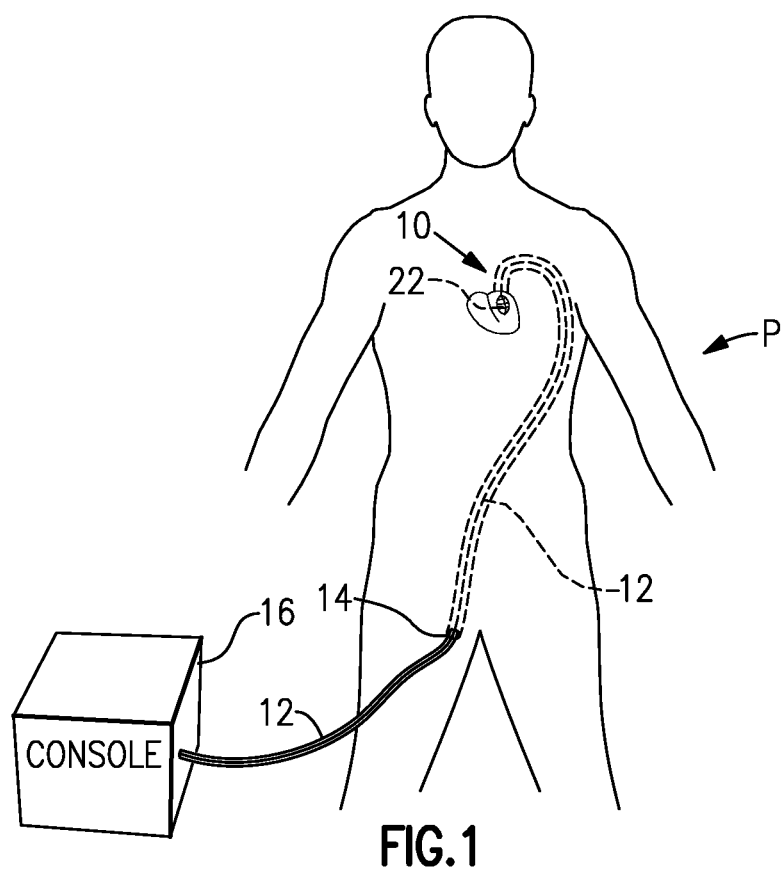
FIG. 1 is a schematic view of a patient in whom is implanted a left-ventricular assistance device or LVAD, according to an embodiment of this invention.

With reference to the Drawing Figures, FIG. 1 illustrates a cardiac patient P in a supine position with a left-ventricle assist device or LVAD 10 inserted into the left ventricle V of the patient's heart. A catheter is inserted via a portal 14 into the patient P's femoral artery, then proceeding up to the patient's aorta and through the aortic valve AV into the chamber of the ventricle. The portal is shown here at the patient's crotch area near the pelvic area. The proximal or outer end of the catheter 12 is connected to an external console 16 which senses the patient's heart rhythm and applies mechanical forces to internal shafts or cannulae within the catheter to control the pumping action of the LVAD 10. In this example, there are conductive pads 18 affixed onto the patient's chest with wires to connect to the console, so that EKG signals are sensed by the console to obtain timing of compression and relaxation the patient's ventricle, i.e., systole and diastole. Alternatively, a pressure sensor or other sensor can be placed at the tip of the catheter and within the patient's ventricle V as a way to pick up the patient's heart beat rhythm.

Figure 3:
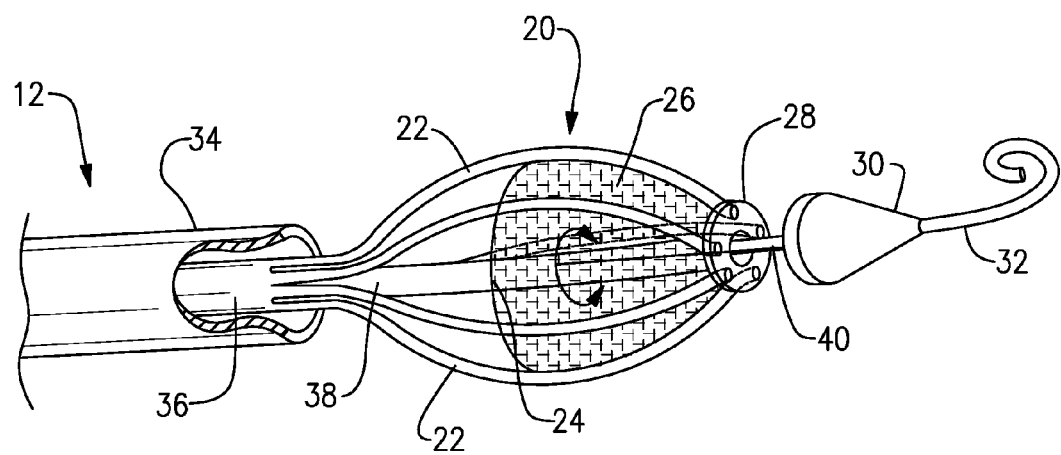
FIG. 3 is an expanded view the capsule portion of the LVAD of this embodiment.
Figure 4:
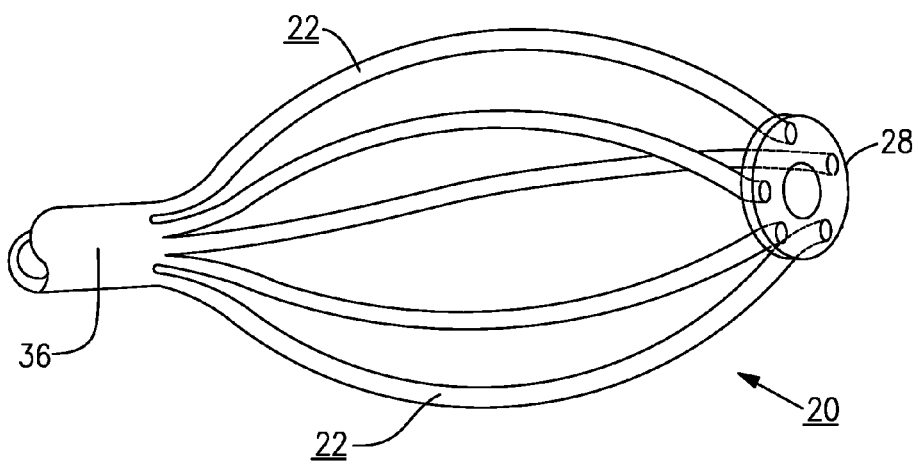
FIG. 4 is a schematic view showing the hollow tubular outer shaft joined with ends of the wires of the cage.

As shown in FIGS. 2, 3 and 4, the LVAD 10 is formed as a generally ovoid or elongated ellipsoid shaped capsule 20 that includes a cage 22 formed of a number of Nitinol wires or other shape-memory material, e.g., a suitable shape-memory flexible polymer. These wires are normally bowed outward, as shown here. A central shaft 24 extends from the catheter through the proximal end of the wire cage 22 to its distal end, where the wires are attached onto a disk or flange 28 affixed on the central shaft 24. A cup or pouch 26, formed of a tough medical grade polymer, and which is flexible but does not stretch, is affixed to the inside of the wire cage 22 and occupies the distal half of the capsule 20, leaving the proximal half open, as shown. An end cap 30 is positioned adjacent the disk 28 at the distal end of the capsule 20. This can be formed of an elastomer or rubber, and a rubber pigtail 32 extends from the end cap and serves as to cushion the distal end of the capsule that may contact the apex of the patient's ventricle.

As shown in more detail in FIG. 3, the catheter 12 has a number of concentric tubular shafts within an outer sheath 34, including an outer tubular shaft 36, and intermediate shaft 38 within the open core of the outer shaft 36, and a central hollow shaft 40 disposed inside the core of the intermediate shaft 38. The individual wires of the cage 22 originate from the distal end of the outer tubular shaft 36 (See FIG. 4), and the central shaft 24 or axle of the capsule 20 is affixed on or unified with the distal end of the intermediate shaft 38. In this embodiment, the outer hollow shaft 36 is at a fixed position in the sheath, and does not rotate nor displace forward or back. The intermediate shaft, however, is free to rotate and displace, so that the central shaft or axle 24 and the disk 28 can twist and can move proximally-distally, so as to create a relative rotation and relative fore-and-aft movement between the proximal and distal ends of the capsule 20. The central hollow shaft 40 proceeds out through the disk or flange 28 and serves as a mounting for the end cap 30 and pigtail 32. The hollow core of the inner or central shaft 40 accommodates the guide wire (not shown) that is used to install the catheter 12 and capsule 20 of the LVAD in the patient's ventricle V. The gap shown in FIG. 3 between the disk 28 and end cap 30 is for purposes of explaining the construction of this embodiment. Normally, the end cap 30 is positioned adjacent or against the disk 28.

As shown in FIGS. 2A and 2B, the central shaft 24 is kept rotated in one direction for diastole (FIG. 2A) so that the cage 22 is fully expanded, and the membrane cup or pouch 26 is also open and expanded to draw in and receive blood coming in through the patient's mitral valve. Then, and the commencement of systole the central shaft 24 is rotated the other direction to twist the cage 22 and compress the pouch 26 (FIG. 2B), and that action pushes blood out from the capsule 20 and out through the patient's aortic valve AV. This increases both the blood volume and velocity flowing into the patient's aorta. The additional velocity creates an entrainment effect to cause enhanced flow of blood already in the artery. The central shaft 24 may also be displaced proximally, i.e., towards the aortal valve AV, during systole, to pull the distal end of the capsule 20 forward, and thus create an additional push to assist blood outflow. At the commencement of diastole, the central shaft 24 and the distal half of the capsule would be displaced distally or towards the apex of the ventricle, and this creates a relative suction to assist in bringing blood from the left atrium into the ventricle.

The action as just described involving displacing and twisting the capsule's cage 22 and its membrane pouch or cup 26 are controlled in the console 16, based on the detection of the patient's heart rhythm, so that the LVAD assists the patient's normal heart action, and does not fight against it. If an arrhythmia is detected, the console can pause the action of the LVAD until the arrhythmia event has ended. Adjustments of the action of the LVAD can also be made on the console by medical staff. The construction and operation of the console may vary, and can incorporate any of the many existing or known techniques and any of the available mechanical and electronic elements that exist.

In this example, the LVAD arrangement of this invention is employed on an immobile patient suffering a significant cardiac weakness or heart failure. However, it is contemplated that versions of this invention could be used or adapted for use in portable or mobile situations, or in some cases could be used by an ambulatory patient with a suitable console or control unit worn on or carried by the patient. The dimensions of the capsule portion of the LVAD can vary for different patients with different size hearts or with different cardiac conditions. Also, in some cases the LVAD could be inserted into a patient's right ventricle, e.g., to assist in flow through the pulmonary blood vessels.

While the present invention has been described with reference to a preferred embodiment and variations thereof, it should be understood that the invention is not limited to those precise embodiments or variations. Rather, many further modifications and variations would present themselves to persons skilled in the art without departure from the scope and spirit of this invention, as defined in the appended claims.

What is claimed is:

1. An endocardial left-ventricle assist device comprising:
   a capsule that is shaped and dimensioned to occupy the space within the left ventricle of a patient's heart, said capsule having a proximal end and a distal end, the distal end being adapted to reside adjacent an apex of the left ventricle of the patient's heart, with the proximal end facing towards the aortal valve of the patient's heart, and the capsule including
      a wire cage formed of a plurality of shape-retaining resilient wires which each extend from the proximal end to the distal end of the capsule;
      a central shaft extending from a proximal end to a distal end of the wire cage and including a flange member at a distal end of the central shaft to which distal ends of the shape-retaining resilient wires are affixed; and
      a cup formed of a flexible but inextensible membrane affixed onto said wires at a distal half of the wire cage, and leaving a proximal half of the wire cage uncovered;
   a catheter configured to extend from outside the patient's body through a major blood vessel and through the patient's aortal valve into the left ventricle of the patient's heart, said catheter including at least an outer tubular shaft onto which proximal ends of said plurality of shape-retaining resilient wires are affixed, a middle tubular shaft affixed to a proximal end of the central shaft of said capsule, an inner tubular shaft extending through the middle tubular shaft and through an open core of said central shaft, and an end cap positioned on said inner shaft on a distal side of said flange member; and
   a control mechanism coupled to the outer tubular shaft and the middle tubular shaft of said catheter, and including means for sensing systole and diastole of the patient's heart, and a mechanism imposing relative rotation as between said outer shaft and said middle shaft in synchronism with the systole and diastole of the patient's heart so as alternately to cause relative rotation in one direction on diastole to open said capsule and allow the cup thereof to fill with blood entering the ventricle and then to cause relative rotation in the opposite direction on systole to twist the wires of said cage around said central shaft so as to squeeze said capsule in a fashion to expel blood from the cup and drive the blood out into the patient's aorta.

2. Endocardial left-ventricle assist device according to claim 1 wherein said capsule is in the form of an oblong ellipsoid.

3. Endocardial left-ventricle assist device according to claim 1 wherein said shape-retaining resilient wires are nitinol wires.

4. Endocardial left-ventricle assist device according to claim 1 wherein said flange member includes a disk affixed at the distal end of said central shaft.

5. Endocardial left-ventricle assist device according to claim 1 further comprising a soft-rubber tip positioned on a distal side of said end cap.

6. Endocardial left-ventricle assist device according to claim 1 wherein said catheter includes a sheath disposed outside said outer tubular shaft.

7. Endocardial left-ventricle assist device according to claim 1 wherein said outer tubular shaft from which the wires of the wire cage extend is movable to extend and retract axially in coordination with rotation of said relative rotation between the outer tubular shaft and the middle tubular shaft and central shaft on which the flange member is mounted.

8. Endocardial left-ventricle assist device according to claim 1 wherein the outer tubular shaft of said catheter and the middle tubular shaft thereof are configured to permit relative displacement therebetween.

* * * * *